US005548115A

United States Patent [19]
Ballard et al.

[11] Patent Number: 5,548,115
[45] Date of Patent: Aug. 20, 1996

[54] PROBE DEVICE FOR DETECTING CONTAMINANTS IN SUBSURFACE MEDIA

[75] Inventors: John H. Ballard, Clinton; Stafford S. Cooper; John C. Morgan, both of Vicksburg, all of Miss.; William R. Lawrence, Dickinson, Tex.; Bobby E. Reed, Vicksburg, Miss.

[73] Assignee: U.S. Army Corps of Engineers as Represented by the Secretary of the Army, Washington, D.C.

[21] Appl. No.: 536,913

[22] Filed: Sep. 29, 1995

[51] Int. Cl.$^6$ ............................ G01N 21/64; G01N 21/88
[52] U.S. Cl. ...................... 250/253; 250/301; 250/458.1; 250/461.1
[58] Field of Search .................................. 250/253, 301, 250/458.1, 461.1

[56] References Cited

U.S. PATENT DOCUMENTS

| | | | |
|---|---|---|---|
| 5,065,019 | 11/1991 | Darilek et al. | 250/461.1 X |
| 5,128,882 | 7/1992 | Cooper et al. | 250/458.1 X |
| 5,246,862 | 9/1993 | Grey et al. | 436/28 |
| 5,461,229 | 10/1995 | Sauter et al. | 250/253 |

Primary Examiner—Carolyn E. Fields
Assistant Examiner—Edward J. Glick
Attorney, Agent, or Firm—Luther A. Marsh

[57] ABSTRACT

A probe device for in-situ detection of contaminants such as petroleum products in a subsurface media such as soil. The device comprises an elongated probe housing which is driven into the media. An ultraviolet lamp located in the housing provides excitation energy which is reflected through a UV transparent window in the housing to the media by at least one reflecting element in the housing. The reflecting element allows longitudinal offset of the lamp from the window providing space for high intensity UV lamps. A radiation receiver receives fluorescent radiation emitted from contaminants in the media transmitted through the window and provides a signal for analysis equipment on the surface. A concentrating reflector between the lamp and the housing and a focusing lens between the lamp and the reflecting element collect and focus excitation energy from the lamp. A filter between the lamp and the first reflecting element filters unwanted wavelengths from the excitation energy and a filter between the window and radiation receiver filters unwanted wavelengths from the radiation receiver. A calibration receiver is positioned in the optical path to receive excitation energy just before exiting the window. The design improves sensitivity, especially for POL contaminants and eliminates the need for complicated excitation equipment at the surface.

21 Claims, 4 Drawing Sheets

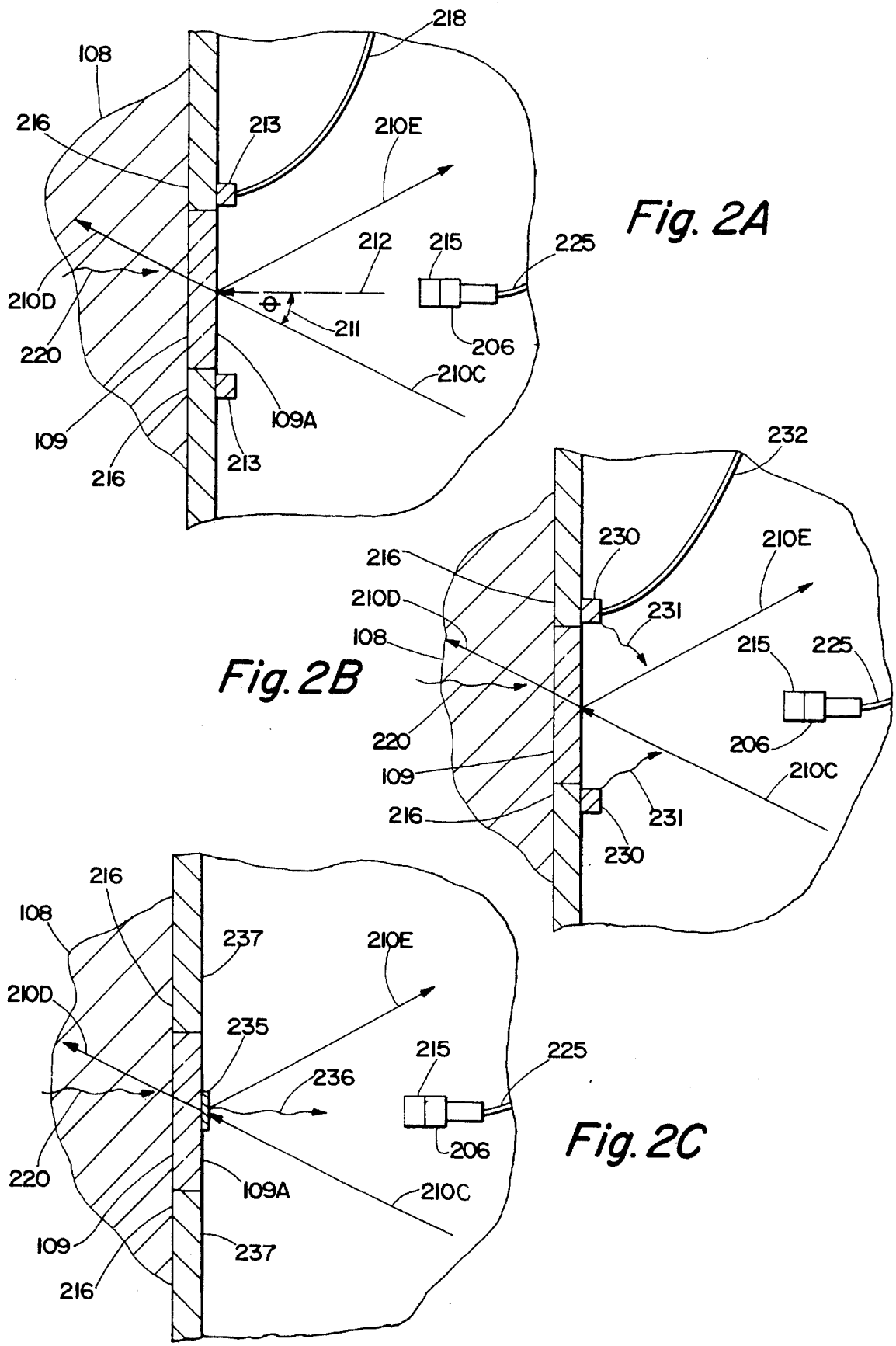

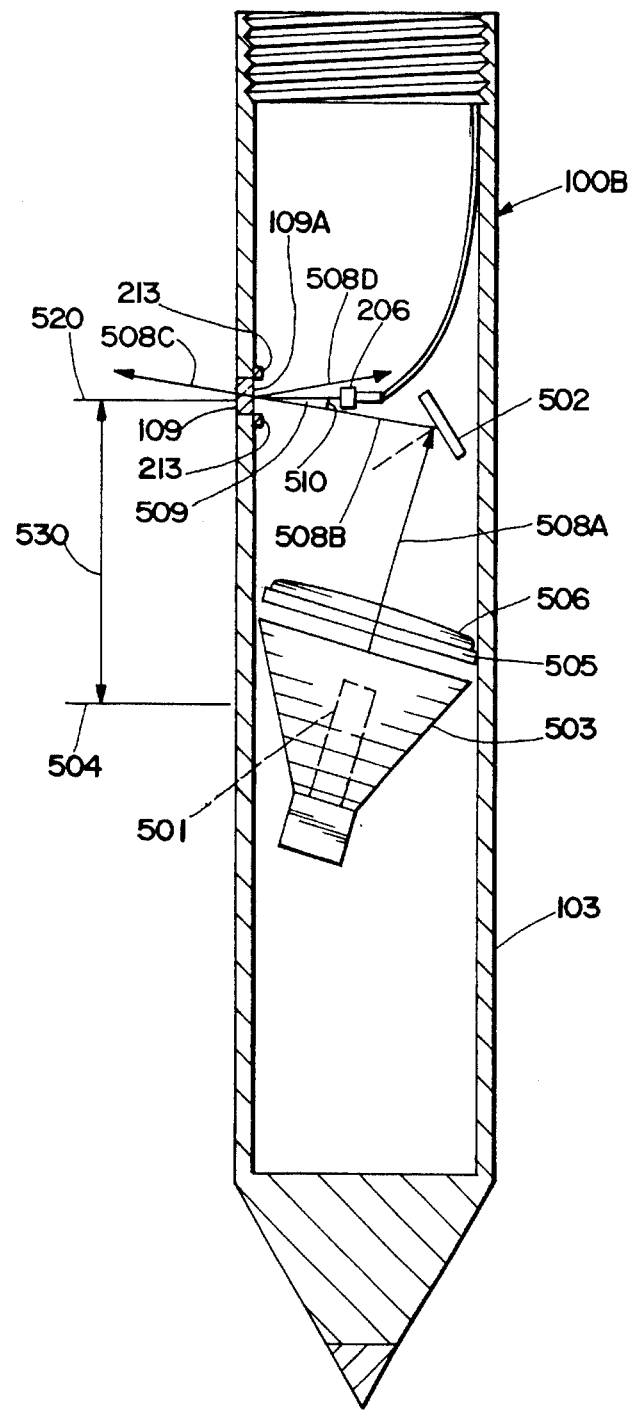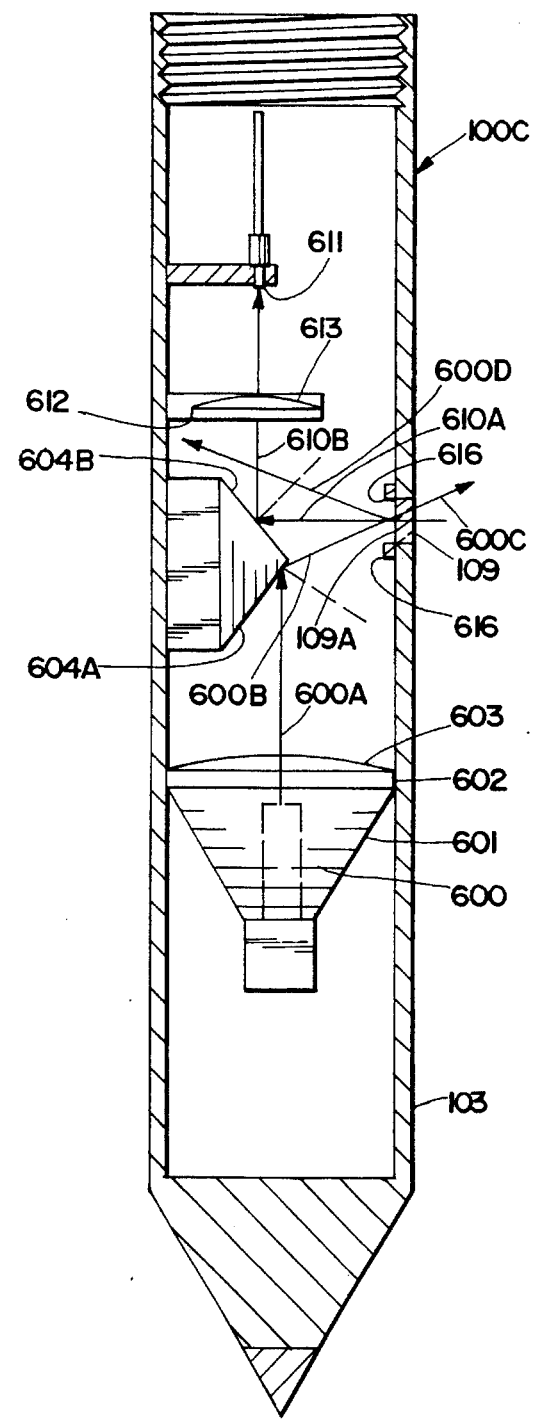
Fig. 4
Fig. 6

PROBE DEVICE FOR DETECTING CONTAMINANTS IN SUBSURFACE MEDIA

STATEMENT OF GOVERNMENT INTEREST

The invention described and claimed herein may be manufactured and used by or for the Government of the United States of America for governmental purposes without the payment of royalties thereon or therefor.

BACKGROUND OF THE INVENTION

The present invention relates to subsurface media or soil contaminant sensing devices and, more particularly, to media probe devices utilizing fluorescence of media contaminants as a sensing means.

In-situ sampling and analysis of media contaminants such as POL (Petroleum, Oil, Lubricants) provides real-time results of contaminant distribution in media strata. Continuous measuring and recording of various media profiles allows testing strategy and mapping to be modified at the site as results dictate. Delays in obtaining results from core samples are eliminated. Drilling wastes associated with core drilling are also eliminated.

Sampling by use of a penetrator probe was disclosed in U.S. Pat. No. 5,128,882 to Cooper et al. The probe is driven into the media by a media penetrator unit. The probe comprises a light transparent window and an ultraviolet (UV) source disposed internally of the probe. Media adjacent to the probe is illuminated by UV energy transmitted from the source through the window. Fluorescent light emitted from contaminants in the media passes through the window and is collected and transmitted to the surface for analysis through a fiber optic link.

Practical application of media probe units is hampered by the limitation in providing adequate intensity UV illumination of the media at the desired wavelength through the window. The diameter of the probe must be kept small to avoid excessive insertion forces. Placement of a UV lamp in the probe opposite the window results in limitations on lamp size and orientation of the lamp. Placement of the fiber optic link is also restricted due to interference from the lamp. Use of a laser source at the surface coupled to the probe with a fiber optic link results in high cost and excessive attenuation of wavelengths less than 290 nanometers by the fiber optic link.

Another problem with existing probe designs is the difficulty to accurately calibrate the devices due to variances in excitation of the contaminants in the media resulting from excitation source intensity variations and optical path variances.

SUMMARY OF THE INVENTION

Therefore an object of the present invention is to provide a probe for penetrating subsurface media utilizing an internal excitation source with an improved optical path to provide increased excitation of desired wavelengths for contaminant sensing, in particular, POL contaminants in subsurface soil.

A further object of the present invention is to provide a probe with source filtering to prevent excitation of the media with undesired wavelengths.

A further object of the present invention is to provide a probe with selectable receiver filtering to improve detection sensitivity in the desired wavelengths.

A further object of the present invention is to provide a probe with a calibration receiver interior to the probe to compensate for excitation source output and optical path variances.

A further object of the present invention is to provide a probe with an active or passive calibration source separate from the excitation source and interior to the probe to provide accurate calibration of analysis equipment.

Yet another object of the present invention is to provide a probe which is economical and reliable to use.

The probe of the present invention comprises an elongated housing comprising a tubular side wall and a penetrator tip at the bottom portion of the housing for penetrating the subsurface media. A source emitting excitation energy for exciting contaminants in the media is located in the interior portion of the housing. A window transparent to the excitation energy and radiation emitted from contaminants in the media is located in the side wall so the window is adjacent to the media when the probe is inserted into the ground or the surface of the media. A reflecting element, such as a mirror, collects the excitation energy from the source and reflects the energy through the window to the media outside the housing. Radiation such as fluorescence from contaminants in the media passes through the window into the interior portion of the housing and is collected by a radiation receiver or waveguide.

The mirror reflects the excitation energy at an angle greater than zero degrees to the normal of the inside surface of the window where the energy strikes the inside surface of the window. The angle is chosen to direct excitation energy reflected from the inside surface of the window away from the radiation receiver inside the housing. The angle between the excitation energy and the normal to the inside surface of the window is less than the critical angle of the window material to reduce attenuation of the excitation energy transmitted through the window to the media.

A calibration receiver is located adjacent to the window at the end of the optical path of the excitation energy to allow detection of variances occurring at the excitation source or any point along the optical path of the excitation energy. The calibration receiver is shielded from stray or reflected excitation energy from outside the housing by the side wall or baffling. An active or passive calibration source separate from the excitation source may be placed inside the housing. Calibration excitation energy emitted by the calibration source and received by the radiation receiver may be used to calibrate spectrum and amplitude analysis equipment.

One or more filters may be placed in an optical path between the excitation source and the window to filter unwanted wavelengths from the excitation energy. Additional filters, including a selectable or tunable filter may also be placed in a second optical path between the window and the radiation receiver to increase sensitivity to desired wavelengths. Additional reflecting elements and focusing elements may be used in the optical paths to collect and concentrate the excitation energy from the excitation source and radiation from the contaminants in the media.

BRIEF DESCRIPTION OF THE DRAWINGS

These and other features, aspects and advantages of the present invention will become better understood with regard to the following description, appended claims and accompanying drawings where:

FIG. 2A is a detail of the window area of FIG. 2 showing the excitation energy striking the inside surface of the window and a calibration arrangement utilizing a calibration receiver;

FIG. 2B is a detail of the window area of FIG. 2 showing an alternative calibration arrangement utilizing an active calibration source within the probe;

FIG. 2C is a detail of the window area of FIG. 2 showing an alternative calibration arrangement utilizing a passive calibration source within the probe;

FIG. 4 is a side elevation, cross sectional schematic drawing of a second embodiment of the probe utilizing a single reflecting element between the excitation source and the window;

FIG. 6 is a side elevation, cross sectional schematic drawing of a third embodiment of the probe utilizing a reflecting element between the window and the radiation receiver.

DESCRIPTION OF THE PREFERRED EMBODIMENTS

Figure 1:
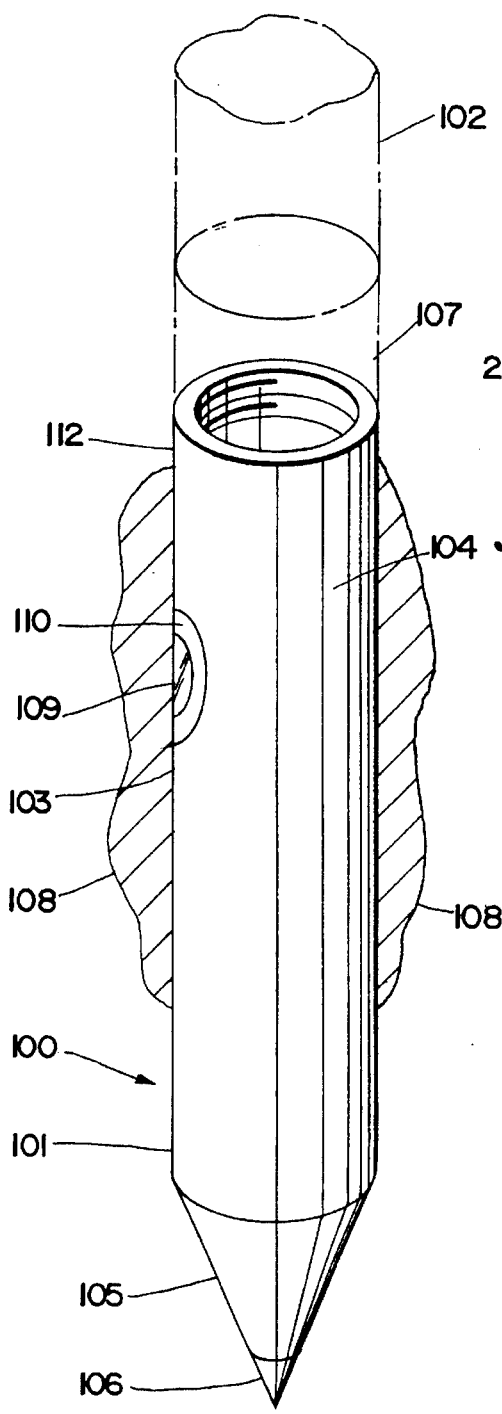
FIG. 1 is a perspective drawing showing the probe inserted into subsurface media by a penetrator rod.

FIG. 1 is a perspective drawing of an embodiment of the present invention in an in-situ testing environment. Probe 100 is inserted into a test location in media 108 by drive rod 102. Elongated probe housing 103 comprises cylindrical side wall 104, conical section 105, and tip 106. Sealing adapter 107 seals housing 103 and provides connection with drive rod 102. Conical section 105 and tip 106 are located at the bottom end 101 of housing 103 to facilitate penetration of the unit into subsurface media 108. Side wall 104, conical section 105, and tip 106 are constructed of a material such as steel with sufficient strength and thickness to allow driving of the housing into media 108 with drive rod 102 without damage to the housing. Media 108 surrounds wall 104 when probe 100 is inserted into the media. Window 109 is located in side wall 104 and is retained in the wall by threaded retaining ring 110. Window 109 is substantially coplanar with side wall outside surface 112 to minimize damage to window 109 while maintaining contact with media 108 during insertion in media 108.

Figure 2:
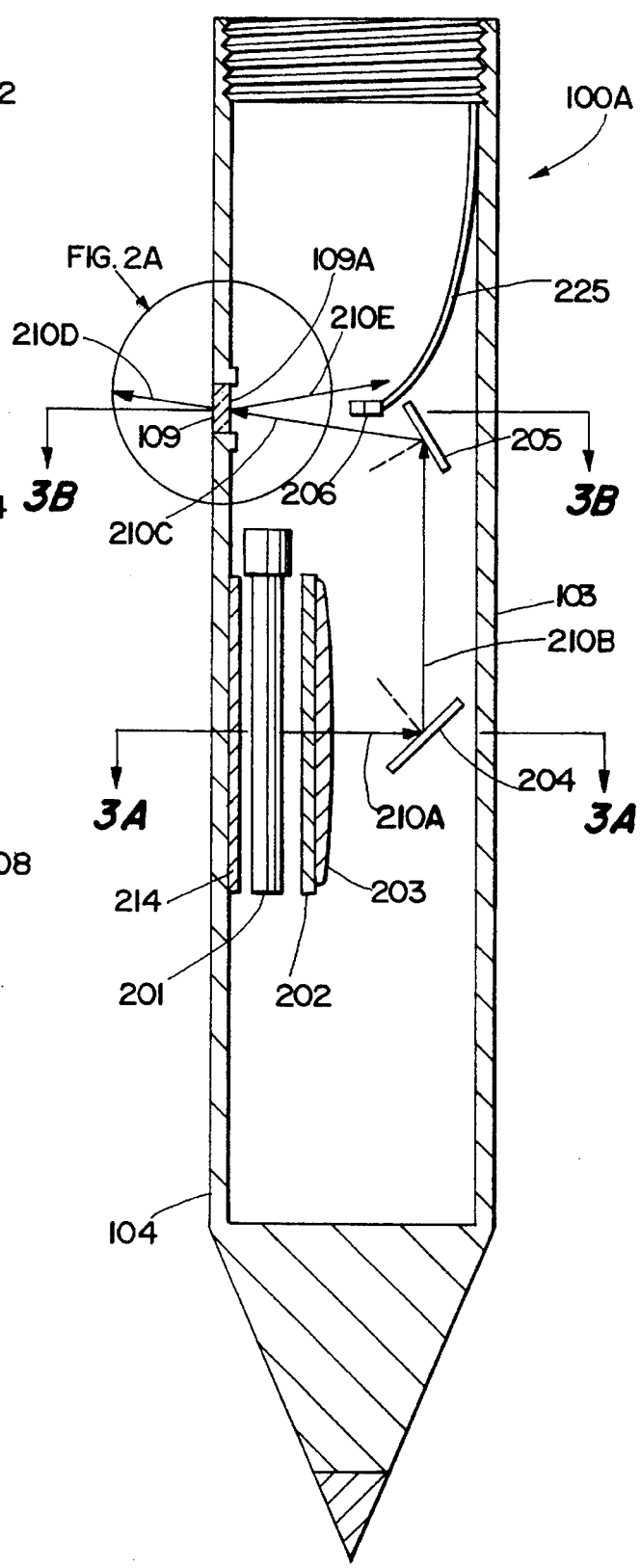
FIG. 2 is a side elevation, cross sectional schematic drawing of a first embodiment of the probe.

FIG. 2 is a side elevation, cross sectional schematic drawing of probe embodiment 100A. An excitation source such as UV lamp 201 is located in the lower portion of housing 103. Excitation energy 210A from lamp 201 passes through filter 202 and is collected and focused by a focus element such as lens 203 and is directed to a reflecting element such as mirror 204. Excitation energy 210B is reflected from mirror 204 to mirror 205. Excitation energy 210C reflected from mirror 205 strikes inside surface 109A of window 109 and a portion, energy 210D, is transmitted through window 109 and excites fluorescence or radiation in media 108 outside housing 103 if suitable compounds such as petroleum contaminates (not shown) are present.

Referring to FIG. 2A, radiation receiver or waveguide 206 is located opposite window 109 to receive radiation 220 from contaminants in media 108 outside window 109. Excitation energy 210E reflected off inside window surface 109A and striking waveguide 206 is reduced by positioning mirrors 204 and 205 of FIG. 2 so that excitation energy 210C strikes inside surface 109A of window 109 at angle 211 from normal 212. Normal 212 is taken at the point of contact of energy 210C on inside surface 109A. Angle 211 is chosen to be greater than zero degrees to reflect energy 210E away from waveguide 206. Excitation energy 210E striking waveguide 206 is undesirable because it reduces sensitivity to radiation 220 from contaminants in media 108.

Angle 211 is chosen to be less than the critical angle to minimize attenuation of energy 210D through window 109. The critical angle $\phi$ is defined as:

$$\phi = \mathrm{asin}\,(n_2/n_1)$$

where $n_1$ is the index of refraction of the internal medium (normally air at ambient pressure) in the interior portion of the housing and $n_2$ is the index of refraction of the window material. In order to retain acceptable excitation energy transmission through the window, the incident angle should be less than the critical angle for the window material in the internal medium. The optimum incident angle is dependent on the optical geometry of the system. In the preferred embodiment, angle 211 is less than 12 degrees for a sapphire window when the internal medium of the probe is air at ambient pressure. Mirrors 204 and 205 may be front surface mirrors to reduce scattering, absorption and multiple reflection of excitation energy in the mirror.

The placement of lamp 201 of FIG. 2 in the lower portion of housing 103 below window 109 allows use of a larger, more powerful lamp due to less interference with other components such as waveguide 206. The longer optical path achieved in this placement allows greater focusing distance to converge the collected excitation energy through window 109. The increased convergence of the focused excitation energy results in increased excitation intensity and increased sensitivity to media contaminants. In one embodiment, lamp 201 is a mercury vapor gas discharge lamp. In an alternative embodiment, other UV radiation sources may be used such as a deuterium lamp depending on the desired wavelength spectrum of the excitation. Multiple lamps may be used to produce additional intensity or additional wavelengths to detect additional contaminants.

Fiber optic waveguide 206 receives radiation and reflected/scattered energy from contaminants in media 108 outside housing 103 and transmits them to spectrum analysis equipment on the surface for analysis. A filter such as tunable filter 215 of FIG. 2A may be placed at the receptor end of waveguide 206 to filter unwanted wavelengths. Filter 215 increases the sensitivity of probe 100A by filtering stray and reflected excitation and masking radiation from contaminants in media 108. Although fluorescence is the primary mode of sensing for contaminants, spectrum analysis of reflected radiation received by waveguide 206 may be used to analyze components and contaminants in media 108.

Calibration receiver 213 is positioned inside probe 100A adjacent to inside window surface 109A. In this position, calibration receiver 213 receives source excitation energy 210C from lamp 201 as a result of energy 210C divergence and scattering.

Calibration receiver 213 is shielded from radiation 220 by side wall portion 216 or by internal baffling (not shown). Calibration receiver 213 is coupled to surface instrumentation by fiber optic cable 218. Analysis of the amplitude and spectrum of the excitation received by calibration receiver 213 allows calibration of the signal received from waveguide 206. Placement of calibration receiver 213 near the inside surface of window 109 allows calibration receiver 213 to respond to most factors affecting amplitude and wavelength of the received energy spectrum including lamp 201 fluctuations and optical path variances caused by temperature effects, misalignments and mechanical stresses on probe 100A. Shielding of calibration receiver 213 from radiation 220 improves the accuracy of the calibration by excluding wavelengths from radiation external to the probe.

FIG. 2B is a detail of an alternative calibration arrangement utilizing an active calibration source 230. Calibration source 230 emits calibration radiation 231 which is received by waveguide 206, which in turn is used to calibrate spectrum analysis equipment on the surface. Active calibration source 230 may radiate energy received through optic link 232 or, alternatively, source 230 may be an active emitter such as a lamp or LED.

FIG. 2C is a detail of yet another calibration arrangement utilizing passive calibration source 235. Calibration source 235 emits calibration radiation 236 when excited by excitation energy 210C. Waveguide 206 receives calibration radiation 236 and transmits it to the surface for calibration of spectrum analysis equipment. Passive calibration source 235 may be a fluorescent paint applied to inside window surface 109A. Alternatively, the fluorescent paint may be applied to interior surface 237 adjacent to inside window surface 109A.

Filter 202 of FIG. 2 eliminates unwanted wavelength emissions from lamp 201. Elimination of these unwanted wavelengths prevents masking of radiation emissions from contaminants in the media, thereby increasing the sensitivity of the sensor. Filter 202 may be a single optical filter, a tunable filter or a combination of filters to eliminate the undesired wavelengths.

Focus element or lens 203 collects and concentrates the excitation energy from lamp 201 and directs the energy to first mirror 204. Lens 203 may be a conventional positive lens or a freshnel type lens. Lens 203 must be transparent to the desired excitation wavelengths.

Concentrating reflector 214 located on the inside of side wall 104 of probe 100A collects and concentrates excitation energy emitted by lamp 201. Reflector 214 may be a UV reflective coating on the inside wall of probe 100 or it may be a separate reflector positioned opposite of lamp 201 from reflecting element 204.

Figure 3A:
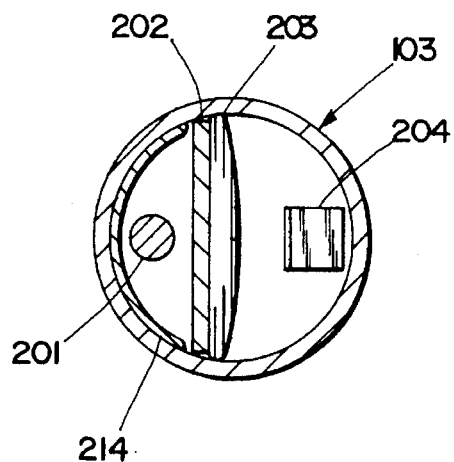
FIG. 3A is a cross sectional schematic drawing of the first embodiment of the probe taken at section 3A—3A of FIG. 2.
Figure 3B:
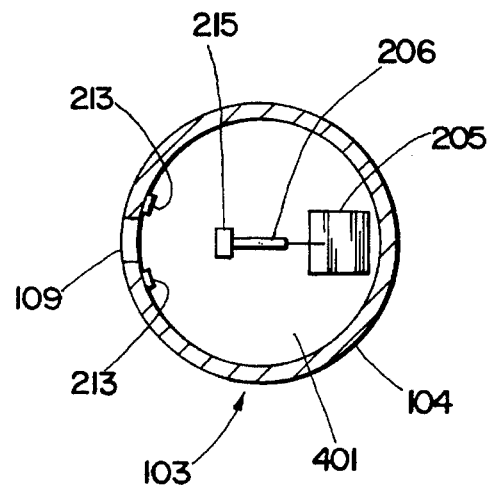
FIG. 3B is a cross sectional schematic drawing of the first embodiment of the probe taken at section 3B—3B of FIG. 2.

FIG. 3A is a plan cross section of probe 100A taken at 3A—3A of FIG. 2, showing the position of lamp 201, concentrating reflector 214, filter 202, lens 203 and mirror 204. FIG. 3B is a plan cross section of probe 100A taken at 3B—3B of FIG. 2 showing the position of mirror 205, window 109, fiber optic waveguide 206, calibration receiver 213 and tunable filter 215. Side wall 104 of housing 103 is a cylindrical tube forming a hollow interior portion 401 to house the interior components. In alternative embodiments, side wall 104 may have polygonal cross sections.

FIG. 4 is a side elevation cross section of probe embodiment 100B utilizing a single reflecting element or mirror 502 between the excitation source or lamp 501 and window 109. Lamp 501 is positioned in the lower interior portion of housing 103 at longitudinal position 504 and optical components including reflector 503, filter 505 and focusing lens 506 are mounted below window 109 at an angle to direct excitation energy 508A towards mirror 502. Mirror 502 reflects energy 508B to window inside surface 109A at angle 509 to normal 510 of window inside surface 109A. A portion of energy 508B, energy 508C, is transmitted through window 109 exciting contaminants in media 108 (not shown). Angle 509 is chosen to be greater than zero degrees to cause energy 508D reflected from window inside surface 109A to avoid waveguide 206. Angle 509 is selected to be less than the critical angle to minimize attenuation of energy 508C as discussed in the previous embodiment. Calibration receiver 213 receives excitation energy from divergence of beam 508B.

Longitudinal position 520 of window 109 in housing 103 is above longitudinal position 504 of lamp 501. In alternative embodiments, longitudinal position of the lamp 501 is above the longitudinal position of window 109. Longitudinal displacement 530 between lamp 501 and window 109 afforded by reflecting element 502 allows larger lamp dimensions and flexibility in placement of the lamp as compared to placement of the lamp opposite to window 109.

Figure 5A:
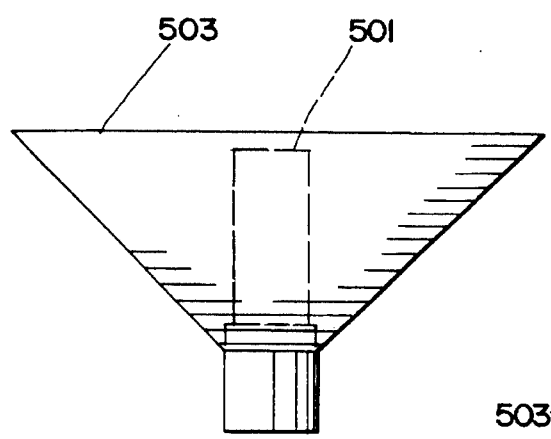
FIG. 5A is a side elevation schematic drawing of the lamp and concentrating reflector of the second embodiment of FIG. 4.
Figure 5B:
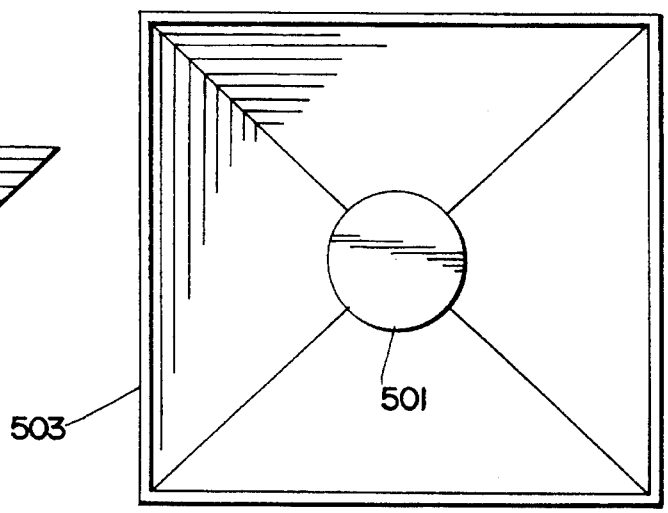
FIG. 5B is a plan view schematic drawing of the lamp and concentrating reflector of the second embodiment of FIG. 4.

FIG. 5A is a side elevation drawing of lamp 501 and reflector 503 of FIG. 4. FIG. 5B is a plan drawing of lamp 501 and reflector 503. Reflector 503 may be of parabolic configuration.

FIG. 6 is a third embodiment showing probe 100C. Excitation energy 600A, emitted by lamp 600, is filtered by filter 602 and concentrated and focused by reflector 601 and lens 603 to mirror 604A. Mirror 604A reflects excitation energy 600B to inside surface 109A of window 109. Energy 600C is transmitted through window 109 to excite contaminants in the media (not shown). Fluorescent radiation 610A from outside housing 103 is transmitted through window 109 to mirror 604B. Mirror 604B reflects radiation 610B into fiber optic waveguide 611. Undesired wavelengths are filtered from radiation 610B by filter 612. Focus element or lens 613 collects and focuses radiation 610B into waveguide 611. Mirror 604A is positioned to direct energy 600B at an angle to the normal of the inside surface of window 109 as discussed in the previous embodiments to reduce illumination of waveguide 611 by energy 600D.

Calibration receiver 616 is adjacent to window 109 and receives excitation from lamp 601 as discussed in embodiment 100A. Calibration receiver 616 may also be a fiber optic waveguide for transmitting the received excitation to the surface for analysis or it may be a discrete radiation sensor such as a photocell. Alternatively, a calibration source may be used in place of calibration receiver 616 as discussed previously.

Window 109 of FIG. 2 may be constructed of sapphire. Other materials may be used which are transparent to the desired UV excitation source and the fluorescent wavelengths of contaminants of interest. Window 109 material must also have sufficient hardness to resist scratching during insertion and retraction from the media.

Alternative embodiments of the present invention can employ more than two reflecting elements to allow longitudinal offsetting of the UV excitation source from the window. The reflecting elements may be focusing or non-focusing. Additional beam forming elements may be inserted into the optical path to condition the energy as desired. Excitation sources at wavelengths other than UV, such as visible or infrared, may be used depending on the contaminants being investigated.

Accordingly the reader will see that the Probe Device For Detecting Contaminants In Subsurface Media provides a probe for in-situ testing for contaminants in media. The device provides the following additional advantages:

the device provides an excitation optical path allowing increased excitation of the media for increased sensitivity in detecting contaminants in the media;

low cost lamps located in the probe housing may be used for excitation, eliminating the requirement for expensive and bulky excitation equipment on the surface;

placement of the calibration receiver at the end of the excitation optical path allows correction for lamp variations and optical path variations;

use of a calibration source in the probe allows calibration of analysis equipment for increased accuracy in detecting contaminants; and excitation source and receiver filtering increases sensitivity for contaminants.

Although the description above contains many specifications, these should not be construed as limiting the scope of the invention but as merely providing illustrations of some of the presently preferred embodiments of this invention. Thus the scope of the invention should be determined by the appended claims and their legal equivalents, rather than by the examples given.

What is claimed is:

1. A probe device for detecting contaminants in a subsurface media, the device comprising:

an elongated housing for penetrating the media, the housing comprising a generally tubular side wall and a penetrator tip at a bottom end of the housing, the housing comprising an interior portion so that the media is outside and surrounding the side wall when the device is inserted into the media;

an excitation source located in the interior portion of the housing, the excitation source emitting an excitation energy;

a window located in the side wall, the window being transparent to the excitation energy;

a first reflecting element located in the interior portion of the housing, the first reflecting element positioned in an optical path between the excitation source and the window to receive a first portion of the excitation energy from the excitation source and reflect a second portion of the excitation energy to the window, a third portion of the excitation energy being transmitted through the window and exciting the contaminants in the media outside of the housing; and a radiation receiver positioned in the interior portion of the housing to receive radiation emitted by the contaminants in the media.

2. The device of claim 1 wherein the window comprises a first window material, the interior portion comprises a first internal medium and wherein the first reflecting element is positioned to reflect the second portion of the excitation energy to the window at a first angle, the first angle being greater than zero degrees to a normal axis of an inside surface of the window at a point of contact with the second portion of the excitation energy and wherein the first angle is less than a critical angle for the first window material in the first internal medium.

3. The device of claim 2 wherein the first window material is sapphire, the first internal medium in the probe is air, and the first angle is less than 12 degrees.

4. The device of claim 1 comprising a calibration receiver in the interior portion of the housing, the calibration receiver positioned adjacent to the window to receive a fourth portion of the excitation energy, the fourth portion of the excitation energy being divergence of the second portion of the excitation energy, and wherein the calibration receiver is shielded from the radiation emitted by the contaminants in the media.

5. The device of claim 1 comprising a calibration source in the interior portion of the housing, the calibration source emitting a calibration radiation and wherein the calibration radiation is received by the radiation receiver.

6. The device of claim 5 wherein the calibration source is connected by an optic link to source equipment external to the probe device.

7. The device of claim 5 wherein the calibration source emits the calibration radiation when excited by the excitation energy.

8. The device of claim 7 wherein the calibration source comprises a fluorescent paint applied to an inside surface of the housing wherein the fluorescent paint is excited by the second portion of the excitation energy.

9. The device of claim 7 wherein the calibration source comprises a fluorescent paint applied to an inside surface of the window and the fluorescent paint is excited by the second portion of the excitation energy.

10. The device of claim 1 wherein the excitation source comprises a lamp capable of emitting ultraviolet radiation.

11. The device of claim 10 comprising a filter in the optical path between the excitation source and the window thereby filtering the excitation energy.

12. The device of claim 11 comprising a concentrating reflector in the interior of the housing opposite the first reflecting element from the excitation source to reflect the excitation energy from the excitation source to the first reflecting element.

13. The device of claim 12 comprising a focusing element in the optical path between the excitation source and the window to collect and focus the excitation energy.

14. The device of claim I comprising a second reflecting element, the second reflecting element disposed in a first portion of the optical path between the excitation source and the first reflecting element, the second reflecting element collecting the excitation energy and reflecting the first portion of the excitation energy to the first reflecting element.

15. The device of claim 1 comprising a radiation reflecting element located in the interior of the housing and positioned to receive the radiation emitted by the contaminants in the media through the window and reflect the radiation to the radiation receiver.

16. The device of claim 1 comprising a filter positioned between the window and the radiation receiver to pass selectable wavelengths of the radiation from the window to the radiation receiver.

17. A probe device for detecting contaminants in a subsurface media, the device comprising:

an elongated housing for penetrating media, the housing comprising a generally tubular side wall and a penetrator tip at a bottom end of the housing, the housing comprising an interior portion and wherein the media is outside and surrounding the side wall when the device is inserted into the media;

an excitation source located at a first longitudinal position of the housing, the excitation source emitting an excitation energy;

a window located in the side wall at a second longitudinal position of the housing, the second longitudinal position being displaced longitudinally from the first longitudinal position, the window being transparent to the excitation energy;

a first reflecting element located in the interior portion of the housing, the first reflecting element positioned to receive a first portion of the excitation energy from the excitation source and reflect a second portion of the excitation energy to the window, a third portion of the excitation energy being transmitted through the window and exciting the contaminants in the media outside of the housing; and a radiation receiver positioned in the interior portion of the housing to receive radiation emitted by the contaminants in the media.

18. The device of claim 17 wherein the window comprises a first window material, the interior portion comprises a first internal medium and wherein the first reflecting element is positioned to reflect the second portion of the excitation energy to the window at a first angle, the first angle being greater than zero degrees to a normal axis of an inside surface of the window at a point of contact with the second portion of the excitation energy and wherein the first angle is less than a critical angle for the first window material in the first internal medium.

19. The device of claim 17 comprising a calibration receiver in the interior portion of the housing, the calibration receiver positioned adjacent to the window to receive a fourth portion of the excitation energy, the fourth portion of the excitation energy being divergence of the second portion of the excitation energy, and wherein the calibration receiver is shielded from the radiation emitted by the contaminants in the media.

20. The device of claim 17 comprising a radiation reflecting element located in the interior of the housing and positioned to receive the radiation emitted by the contaminants in the media passing through the window and reflect the radiation to the radiation receiver.

21. A probe device for detecting contaminants in a subsurface media, the device comprising:

an elongated housing for penetrating media, the housing comprising a generally tubular side wall and a penetrator tip at a bottom end of the housing, the housing comprising an interior portion comprising a first interior medium and wherein the media is outside and surrounding the side wall when the device is inserted into the media;

an ultraviolet lamp located at a first longitudinal position of the housing, the lamp emitting an ultraviolet energy;

a window comprising a first window material, the window located in the side wall at a second longitudinal position of the housing, the second longitudinal position being displaced longitudinally from the first longitudinal position, the window being transparent to the ultraviolet energy;

a first reflecting element located in the interior portion of the housing, the first reflecting element positioned in a first optical path between the lamp and the window to receive a first portion of the ultraviolet energy from the lamp and reflect a second portion of the ultraviolet energy to the window, a third portion of the ultraviolet energy being transmitted through the window and exciting the contaminants in the media outside of the housing, and wherein the first reflecting element is positioned to reflect the second portion of the ultraviolet energy to the window at a first angle, the first angle being greater than zero degrees to a normal axis of an inside surface of the window at a point of contact with the second portion of the ultraviolet energy and wherein the first angle is less than a critical angle for the first window material in the first internal medium;

a fiber optic waveguide disposed in the interior portion of the housing to receive radiation emitted by the contaminants in the media transmitted through the window;

a first filter disposed in the first optical path between the lamp and the window, the first filter filtering undesired wavelengths from the lamp; and a second filter disposed in a second optical path between the window and the fiber optic waveguide, the second filter filtering undesired radiation emitted by the contaminants in the soil.

* * * * *